United States Patent [19]

Cheung et al.

[11] Patent Number: 5,625,101
[45] Date of Patent: Apr. 29, 1997

[54] CYCLODIMERIZATION OF BUTADIENE

[75] Inventors: Tin-Tack P. Cheung; Marvin M. Johnson, both of Bartlesville, Okla.

[73] Assignee: Phillips Petroleum Company, Bartlesville, Okla.

[21] Appl. No.: 497,004

[22] Filed: Jun. 30, 1995

[51] Int. Cl.$^6$ ................................................ C07C 2/46
[52] U.S. Cl. .................................... 585/369; 585/366
[58] Field of Search ........................ 585/366, 369

[56] References Cited

U.S. PATENT DOCUMENTS

| | | | |
|---|---|---|---|
| 2,544,808 | 3/1951 | Stahly | 260/666 |
| 3,444,253 | 5/1969 | Reimlinger et al. | 260/666 |
| 3,497,462 | 2/1970 | Kruerke | 252/454 |
| 4,125,483 | 11/1978 | Downing et al. | 252/455 R |
| 4,384,153 | 5/1983 | Dessau | 585/366 |
| 4,413,154 | 11/1983 | Dessau | 585/366 |
| 4,665,247 | 5/1987 | Dessau | 585/361 |
| 5,043,504 | 8/1991 | Bedell | 585/369 |
| 5,135,620 | 8/1992 | Brown | 203/57 |
| 5,196,621 | 3/1993 | Diesen et al. | 585/361 |
| 5,329,057 | 7/1994 | Diesen et al. | 585/366 |
| 5,488,020 | 1/1996 | Diesen et al. | 585/366 |
| 5,545,789 | 8/1996 | Duisters et al. | 585/508 |

*Primary Examiner*—Ellen M. McAvoy
*Attorney, Agent, or Firm*—Richmond, Phillips, Hitchock & Fish

[57] ABSTRACT

1,3-butadiene is cyclodimerized to 4-vinylcyclohexene in the presence of at least one copper(I) sulfonate as the catalyst.

14 Claims, No Drawings

CYCLODIMERIZATION OF BUTADIENE

BACKGROUND OF THE INVENTION

This invention relates to a process for cyclodimerizing 1,3-butadiene to 4-vinylcyclohexene in the presence of a copper(I) compound as the catalyst.

The use of organic Cu(I) compounds as catalysts for cyclodimerizing 1,3-butadiene to 4-vinylcyclohexene is described in U.S. Pat. No. 2,544,808. The present invention is an improvement of this process resulting in higher butadiene conversion and enhanced selectivity to 4-vinylcyclohexene.

SUMMARY OF THE INVENTION

It is an object of this invention to provide a process for catalytically cyclodimerizing 1,3-butadiene to 4-vinylcyclohexene (4-VCH) at a high selectivity. Other objects and advantages will become apparent from the detailed description and the appended claims.

In accordance with this invention, a feed comprising 1,3-butadiene is contacted with a catalyst comprising at least one copper(I) sulfonate in a reaction zone at effective cyclodimerization conditions to produce 4-vinylcyclohexene (4-VCH). Preferably, the at least one copper(I) sulfonate is dissolved in a solvent (more preferably at least one hydrocarbon solvent).

In one preferred embodiment, the at least one dissolved copper(I) sulfonate is formed by contacting a solution of at least one sulfonic acid with a solid copper(I) oxide-containing material. In a particularly preferred embodiment, a solution comprising at least one sulfonic acid and a feed stream comprising 1,3-butadiene are concurrently passed through a bed of a solid copper(I) oxide-containing material so as to form at least one dissolved copper(I) sulfonate which acts as the catalyst for the production of 4-vinylcyclohexene (from 1,3-butadiene). Preferably, unconverted 1,3-butadiene is separated from 4-VCH (and also from a Cu(I) sulfonate-containing solution, if present) by fractional distillation.

DETAILED DESCRIPTION OF THE INVENTION

Any feed stream comprising 1,3-butadiene can be used in the cyclodimerization process of this invention. The feed stream can consist essentially of 1,3-butadiene, or it can comprise 1,3-butadiene (generally at a volume percentage ranging from about 1% to about 99%, preferably about 10–90%) and other hydrocarbons (in particular butanes and butenes) as the remainder. The feed stream may be liquid or gaseous.

Effective cyclodimerization reactions generally comprise a reaction temperature in the range of about 80° C. to about 200° C. (preferably about 120°–170° C.) and a reaction pressure in the range of about 50–500 psig (preferably about 120–300 psig). Generally, the reaction time is about 0.1–20 hours. The 1,3-butadiene-containing feed stream can be contacted with the Cu(I) sulfonate catalyst in any suitable manner. If the Cu(I) sulfonate is solid, the 1,3-butadiene-containing feed stream generally is passed through a catalyst layer comprising at least one Cu(I) sulfonate. If as is presently preferred, the at least one Cu(I) sulfonate is dissolved in a solvent (generally in at least one aromatic hydrocarbon such as benzene, toluene, xylenes), means for mixing the feed stream comprising 1,3-butadiene and the solution comprising Cu(I) sulfonates are provided. Generally, the concentration of the at least one Cu(I) sulfonate in this solution is about 0.005–1.0 mol/l (preferably about 0.05–0.5 mol/l).

In a particularly preferred embodiment, a feed stream comprising 1,3-butadiene and a solution of at least one sulfonic acid (generally dissolved in an organic solvent such as benzene, toluene and/or xylenes) are passed substantially simultaneously through a layer of a porous solid material comprising copper(I) oxide. More preferably, this solid material is provided by reduction of a solid copper (II) oxide-containing material, in particular CuO/ZnO (having a CuO:ZnO weight ratio of about 1:20 to about 20:1, as is described in U.S. Pat. No. 4,593,148), preferably by heating the material in nitrogen gas for about 4–16 hours at a temperature of about 250°–350° C., wherein a substantial portion of CuO is converted to $Cu_2O$ and $O_2$ gas. When the 1,3-butadiene containing feed stream and the sulfonic acid-containing solution are passed through the at least partially decomposed ("prereduced") copper(II) oxide-containing material (in particular prereduced CuO/ZnO), the dissolved sulfonic acid reacts with $Cu_2O$ (now present in the prereduced material) and forms Cu(I) sulfonate, which is then dissolved in the sulfonic acid-containing solution and almost instantly acts as a catalyst for the cyclodimerization of 1,3-butadiene (present in the feed stream) to form 4-VCH. It is within the scope of this invention to have a desiccant present (either admixed with or placed just downstream of the $Cu_2O$-containing material) to absorb formed water.

The produced effluent exiting the dicyclodimerization reaction zone comprises (i) unreacted 1,3-butadiene, (ii) 4-VCH as the desired product, and (iii) the solution comprising at least one Cu(I) sulfonate (and generally also excess sulfonic acid). These three components are then separated, generally by fractional distillation, wherein the overhead stream contains primarily (i.e., over 50%) unconverted 1,3-butadiene, a sidedrawn stream contains primarily 4-VCH, and a bottom stream contains primarily the solution comprising Cu(I) sulfonate (and generally also unconverted sulfonic acid). The overhead and bottom streams are generally recycled to the cyclodimerization zone. Preferably, the bottom stream is dried to remove therefrom water which has been formed by the reaction of the sulfonic acid(s) and $Cu_2O$. This can be accomplished by passing the bottom stream through a desiccant bed (e.g., silica gel, $CaCl_2$ etc.) before it is recycled. In the above-described, particularly preferred embodiment employing a layer of prereduced CuO/ZnO, generally some sulfonic acid is added to the recycle bottom stream to ensure that enough free sulfonic acid is present in the solution (generally at least about 0.005–0.05 mole of free acid per liter solution) to react with the $Cu_2O$ component of the solid layer (preferably prereduced CuO/ZnO) and to maintain a substantially constant concentration of at least one dissolved Cu(I) sulfonate (the catalyst for converting 1,3-butadiene to 4-VCH) in the solution.

Any suitable sulfonic acid can be employed to make the at least one Cu(I) sulfonate which is employed as the catalyst in the cyclodimerization of this invention. Preferred hydrocarbonsulfonic acids (disclosed in U.S. Pat. Nos. 4,400,564 and 5,135,620) include alkanesulfonic acids containing 4–22 carbon atoms per molecule and aromatic sulfonic acids containing 6–22 carbon atoms per molecule.

Alkanesulfonic acids useful in the practice of this invention can be straight-chained or branched. Non-limiting examples of suitable alkanesulfonic acids include n-butanesulfonic acid, 2-ethylhexanesulfonic acid, 2-methylnonanesulfonic acid, dodecanesulfonic acid, 2-ethyl-5-n-octyldecanesulfonic acid, n-eicosanesulfonic acid, and mixtures thereof.

Non-limiting examples of aromatic sulfonic acids useful in the practice of this invention include benzene-sulfonic acid, alkylbenzenesulfonic acids wherein the alkyl member generally contains from 1 to 20 carbon atoms, such as p-toluenesulfonic acid, p-dodecylbenzenesulfonic acid, p-hexadecylbenzenesulfonic acid, and the like, naphthalenesulfonic acid, phenolsulfonic acid, naphtholsulfonic acids and halogenbenzenesulfonic acids, such as p-chlorobenzenesulfonic acid, p-bromobenzenesulfonic acid, and mixtures thereof. A presently preferred aromatic sulfonic acid is p-dodecylbenzenesulfonic acids. Commercially available mixtures of o-, m-, and p-dodecylbenzenesulfonic acid can be employed. Preferably, this mixture contains predominantly (i.e., 84–90 mole percent) the para isomer.

Petroleum sulfonic acids which generally comprise a mixture of various alkanesulfonic acids and aromatic sulfonic acids can also be used in the practice of this invention. These petroleum sulfonic acids can be prepared by sulfonation, generally with an $SO_3/SO_2$ mixture, of a deasphalted solvent-refined petroleum fraction having a viscosity of about 140–720 SUS at 210° F.

If the preparation of the Cu(I) sulfonate is carried out in a separate step (before its use as a catalyst in the cyclodimerization reaction), it is generally prepared by refluxing a solution of the sulfonic acid in a suitable diluent, preferably xylene(s), together with cuprous oxide, with a provision for removing the water of reaction, as has been described in U.S. Pat. No. 4,400,564. The preparation is generally carried out in an oxygen-free inert atmosphere, such as under nitrogen, preferably at a molar ratio of sulfonic acid to copper (in the +1 valence state) of about 1:1, for a period of time sufficient to substantially complete the reaction. If desired, the formed copper(I) sulfonate salt can be separated from the diluent, such as by vacuum distillation.

The following examples are provided to further illustrate this invention and are not to be construed as unduly limiting the scope of this invention.

EXAMPLE I

This example illustrates the use of an aromatic Cu(I) sulfonate as a catalyst in the cyclodimerization of 1,3-butadiene to 4-vinylcyclohexene (4-VCH).

7.17 g (0.050 mole) $Cu_2O$ was mixed with 33.3 g (0.106 mole) dodecylbenzenesulfonic acid ($C_{12}H_{25}$—$C_6H_5$—$SO_3H$) dissolved in 150 cc toluene. The mixture was heated for several hours under reflux conditions at 110° C. while a nitrogen stream was passed through the reaction mixture (contained in a stirred glass reflux flask equipped with a condenser). Formed water (about 1.8 cc) was condensed and collected during the reaction. The finished reaction mixture containing the formed Cu(I) dodecylbenzenesulfonate was cooled in a nitrogen atmosphere.

An autoclave reactor was charged with 30 cc of the above-described solution of Cu(I) dodecylbenzenesulfonate in toluene, 34.6 g cyclohexane (as diluent) and 50 g of a mixture containing 60 weight-% 1,3-butadiene and 40 weight-% n-butane. The autoclave was purged with $N_2$, and its contents were stirred and heated to a temperature of about 265°–285° F. (pressure: about 140–200 psig). Samples were taken at periodic intervals for gas chromatographic analyses. After a total reaction time of 11 hours, about 70% of the charged butadiene had been converted, at a selectivity to 4-VCH of 96–97%

EXAMPLE II

This example illustrates the use of Cu(I) salts of other alkyl-substituted benzenesulfonic acid as a catalyst in the cyclodimerization of 1,3-butadiene to 4-VCH.

7.18 g $Cu_2O$ was mixed with 33.6 g of a mixture of linear alkylbenzenesulfonic acids (provided by Alfa Aesar, Ward Hill, Md.) dissolved in 150 cc toluene. The entire mixture was heated under reflux conditions, as has been described in Example I. An autoclave was charged with 30 cc of the formed Cu(I) sulfonate solution, 50.8 g cyclohexane and 62 g of a 60/40 mixture of 1,3-butadiene and n-butane. The autoclave was purged with $N_2$, and its contents were heated to a temperature of about 260°–273° F. (pressure: 140–200 psig). After a total reaction time of about 9 hours, about 53% of the charged 1,3-butadiene had been converted, at a selectivity to 4-VCH of 94–95%.

A control run with solid $Cu_2O$ as the catalyst revealed that the 1,3-butadiene conversion to 4-VCH (at about 260°–290° F. and about 150–190 psig) was only about 10% after a reaction time of about 9 hours.

Reasonable variations, modifications and adaptations for various conditions and reactants can be made within the scope of the disclosure and the appended claims without departing from the scope of this invention.

That which is claimed:

1. A process for converting 1,3-butadiene to 4-vinylcyclohexene which comprises contacting a feed comprising 1,3-butadiene with a catalyst comprising at least one copper(I) sulfonate in a reaction zone at effective cyclodimerization conditions to produce 4-vinylcyclohexene.

2. A process in accordance with claim 1, wherein said at least one copper(I) sulfonate is contained in a solution.

3. A process in accordance with claim 2, wherein the concentration of said at least one copper(I) sulfonate in said solution is in the range of about 0.005–1.0 mole/l.

4. A process in accordance with claim 2, wherein the solvent of said solution is at least one aromatic hydrocarbon.

5. A process in accordance with claim 2, wherein said at least one dissolved copper(I) sulfonate has been formed by contacting a solution of at least one sulfonic acid with a solid copper(I) oxide-containing material.

6. A process in accordance with claim 5, wherein said at least one sulfonic acid is selected from the group consisting of alkanesulfonic acids containing 4–22 carbon atoms per molecule and aromatic sulfonic acids containing 6–22 carbon atoms per molecule.

7. A process in accordance with claim 6, wherein said at least one sulfonic acid is dodecylbenzenesulfonic acid.

8. A process in accordance with claim 5, wherein said solution comprising said at least one sulfonic acid and said feed comprising 1,3-butadiene are concurrently passed through a bed of said solid copper(I) oxide-containing material so as to form said at least one dissolved copper(I) sulfonate in-situ which acts as the cyclodimerization catalyst for the production of 4-vinylcyclohexene from 1,3-butadiene.

9. A process in accordance with claim 1, wherein said feed comprises about 10–90 weight-% 1,3-butadiene.

10. A process in accordance with claim 9, wherein said feed comprises butanes and butenes as the remainder.

11. A process in accordance with claim 1, wherein said effective cyclodimerization conditions comprise a reaction temperature of about 80°–200° C. and a reaction pressure of about 50–500 psig.

12. A process in accordance with claim 11, wherein said reaction temperature is about 120°–170° C. and said reaction pressure is about 120–300 psig.

13. A process in accordance with claim 1, wherein the effluent exiting said reaction zone is subjected to fractional distillation so as to separate unconverted 1,3-butadiene from produced 4-vinylcyclohexene.

14. A process in accordance with claim 1, wherein said at least one copper(I) sulfonate is dissolved in a hydrocarbon solvent, and the effluent exiting a said reaction zone is subjected to fractional distillation so as to obtain an overhead stream comprising primarily unconverted 1,3-butadiene, a sidedrawn stream comprising primarily 4-vinylcyclohexene, and a bottoms stream comprising primarily said at least copper(I) sulfonate dissolved in said hydrocarbon solvent.

* * * * *